United States Patent [19]

Mauric et al.

[11] 4,210,451
[45] Jul. 1, 1980

[54] REGENERATED CELLULOSE FLAMEPROOFED WITH ORGANOPHOSPHORYLAMIDES

[75] Inventors: Claudine Mauric, Basel; Rainer Wolf, Allschwil, both of Switzerland

[73] Assignee: Sandoz Ltd., Basel, Switzerland

[21] Appl. No.: 951,393

[22] Filed: Oct. 16, 1978

Related U.S. Application Data

[63] Continuation of Ser. No. 745,414, Nov. 26, 1976, abandoned, which is a continuation of Ser. No. 520,303, Nov. 4, 1974, abandoned.

[30] Foreign Application Priority Data

| | | |
|---|---|---|
| Nov. 9, 1973 [CH] | Switzerland | 15814/73 |
| Feb. 12, 1974 [CH] | Switzerland | 1934/74 |
| Jun. 10, 1974 [CH] | Switzerland | 7882/74 |
| Jun. 25, 1974 [CH] | Switzerland | 8681/74 |

[51] Int. Cl.² ............................................. C09K 3/28
[52] U.S. Cl. ............................... 106/18.17; 106/18.19; 106/165; 106/168; 106/177; 252/8.1; 264/194
[58] Field of Search ................ 106/15 FP, 16, 17, 18, 106/165, 168, 177, 18.17, 18.15, 18.19; 252/8.1; 260/959, 551 P; 264/194; 8/116 P

[56] References Cited

U.S. PATENT DOCUMENTS

| | | | |
|---|---|---|---|
| 2,953,464 | 9/1960 | Rossin et al. | 106/15 FP |
| 3,083,222 | 3/1963 | Binder et al. | 260/551 P |
| 3,449,161 | 6/1969 | Hindersinn et al. | 260/18 R |
| 3,865,604 | 2/1975 | Riedel et al. | 106/168 |

OTHER PUBLICATIONS

Coover et al., *Ind. & Eng. Chemistry*, "Flame Resistant Polymers", vol. 50, No. 5, 1960, pp. 412-414.

*Primary Examiner*—Lorenzo B. Hayes
*Attorney, Agent, or Firm*—Gerald D. Sharkin; Richard E. Vila; Thomas C. Doyle

[57] ABSTRACT

Flameproofed, regenerated cellulose containing as a flameproofing agent a compound of the formula,

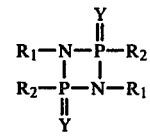

in which
both Y's, are oxygen or sulphur,
both $R_1$'s are cyclohexyl or optionally substituted phenyl, or additionally methyl when Y is sulphur, and
both $R_2$'s are a radical $-NR_3R_4$, wherein
  $R_3$ is hydrogen or alkyl and
  $R_4$ is alkyl, cyclohexyl or optionally substituted phenyl, or
  $R_3$ and $R_4$ together with the common nitrogen atom form a saturated heterocyclic ring, with the proviso that when Y is oxygen, $R_3$ is hydrogen and $R_1$ is optionally substituted phenyl, $R_4$ is only optionally substituted phenyl.

20 Claims, No Drawings

REGENERATED CELLULOSE FLAMEPROOFED WITH ORGANOPHOSPHORYLAMIDES

This is a continuation of application Ser. No. 745,414, filed Nov. 26, 1976, which in turn is a continuation of application Ser. No. 520,303, filed Nov. 4, 1974 both of which prior applications are now abandoned.

The present invention relates to flameproofed, regenerated cellulose and a process for the production thereof with the use of phosphorus-nitrogen heterocyclic compounds as flameproofing agents.

Accordingly, the present invention provides flameproofed, regenerated cellulose containing as a flameproofing agent a compound of formula I,

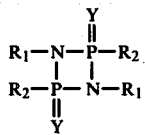
I in which
both Y's are oxygen or sulphur,
both $R_1$'s are cyclohexyl, unsubstituted phenyl or phenyl substituted with up to 3 substituents selected from 1 to 3 chlorine atoms, a bromine atom in the para-position, 1 to 3 $C_{1-4}$ alkyl radicals and 1 to 3 $C_{1-4}$ alkoxy radicals, the aggregate of the carbon atoms in the alkyl and/or alkoxy radicals being a maximum of 4, and, when Y is sulphur, both $R_1$'s may also be methyl, and
both $R_2$'s are a radical of formula

wherein $R_3$ is hydrogen or $C_{1-4}$ alkyl, and
$R_4$ is $C_{1-12}$ alkyl, cyclohexyl, unsubstituted phenyl or phenyl substituted with up to 3 substituents selected from 1 to 3 chlorine atoms, a bromine atom in the paraposition, 1 to 3 $C_{1-4}$ alkyl radicals and 1 to 3 $C_{1-4}$ alkoxy radicals, the aggregate of the carbon atoms in the alkyl and/or alkoxy radicals being a maximum of 4, or
$R_3$ and $R_4$, together with the common nitrogen atom and optionally with a further hetero atom, form a saturated 5- or 6-membered heterocyclic ring,
with the proviso that when simultaneously Y is oxygen, $R_3$ is hydrogen and $R_1$ is unsubstituted or substituted phenyl, $R_4$ is only unsubstituted or substituted phenyl.

In this specification, an "alkyl" radical is a natural or synthesisible primary, secondary or tertiary, or straight or branched-chain alkyl radical, unless stated in specific terms.

Examples of substituted phenyl radicals as signified by $R_1$ and/or $R_4$ are 2-, 3- and 4-methylphenyl, 2-, 3- and 4-chlorophenyl, 4-bromophenyl, 2,3-, 2,4-, 2,5-, 2,6-, 3,4- and 3,5-dichlorophenyl, 2,3-, 2,4-, 2,5-, 2,6-, 3,4-, and 3,5-dimethylphenyl, 2,4,5- and 2,4,6-trimethylphenyl, 2-methyl-4-bromophenyl, 3-methyl-4-bromophenyl, 2-chloro-6-methylphenyl, 3-chloro-2-methylphenyl, 4-chloro-2-methylphenyl, 5-chloro-2-methylphenyl, 2- and 4-ethylphenyl, 2,4-diethylphenyl, o-, m- and p-methoxyphenyl, 3-chloro-4-methoxyphenyl and 3-chloro-6-methoxyphenyl.

Examples of hetero atoms which may be additional to the nitrogen atom in the radical of formula

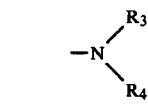

when the latter represents a saturated 5- or 6-membered heterocyclic ring are oxygen, sulphur and nitrogen atoms.

The compounds of formula I embrace the compounds of formula I',

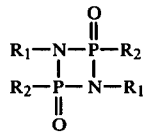
I' in which $R_1$ and $R_2$ are as defined above, and the compounds of formula I'',

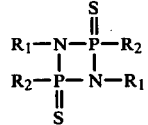
I'' in which $R_1$ and $R_2$ are as defined above.

In both the oxygen-containing (formula I') compounds and the sulphur-containing (formula I'') compounds, the preferred values for $R_1$, on the basis of the flameproofing properties of the appropriate compounds for regenerated cellulose, are unsubstituted and substituted phenyl, and, in the case of the sulphur-containing compounds only, methyl. $R_3$, when not forming with the nitrogen atom and $R_4$ a heterocyclic ring, is preferably hydrogen. $R_4$, for the oxygen-containing compounds, is preferably cyclohexyl, unsubstituted or substituted phenyl or, together with the nitrogen atom and $R_3$, forms a heterocyclic ring, and more preferably is unsubstituted or substituted phenyl, and $R_4$, for the sulphur-containing compounds, is preferably unsubstituted or substituted phenyl.

In the compounds of formula I', any substituted phenyl radical signified by $R_1$ or $R_4$ is preferably phenyl substituted with up to 2 substituents selected from 1 to 2 chlorine atoms and 1 or 2 methyl and ethyl radicals, more preferably phenyl substituted with 1 or 2 chlorine atoms in the meta- and /or para-position(s) or a methyl radical, and most preferably with a methyl radical. In the compounds of formula I'', any substituted phenyl radical signified by $R_1$ is preferably phenyl substituted with 1 or 2 chlorine atoms, a $C_{1-2}$ alkyl or alkoxy radical, or a chlorine atom and a $C_{1-2}$ alkyl or alkoxy radical, more preferably phenyl substituted with 1 or 2 chlorine atoms in the meta- and/or para-position(s), or a methyl or methoxy radical, and most preferably with a chlorine atom in the meta- or para-position or a methyl radical. Any substituted phenyl radical signified by $R_4$ is preferably phenyl substituted with up to 3 substituents selected from 1 or 2 chlorine atoms, a methyl radical and a methoxy radical, more preferably phenyl substituted with 1 or 2 chlorine atoms in the meta- and/or para-position(s), or a methyl or methoxy radical, and most preferably phenyl substituted with a chlorine atom in the meta- or para-position or a methyl radical.

$R_3$, when signifying a $C_{1-4}$ alkyl radical, is preferably methyl or ethyl, and more preferably methyl, for the oxygen-containing compounds, whereas for the sulphur-containing compounds, it is preferably methyl or ethyl. When $R_3$ and $R_4$ together with the common nitrogen atom form a heterocyclic ring, the latter in the case of the oxygen containing compounds is preferably piperidino or morpholino, and in the case of the sulphur containing compounds, preferably piperidino or morpholino, and more preferably piperidino. When $R_4$ signifies an alkyl radical, this is preferably $C_{1-6}$ alkyl.

Of the compounds of formula I', a preferred class is constituted by those of formula I'a, $$R_{1a}'-N-\overset{\overset{O}{\|}}{P}-R_{2a}' \atop R_{2a}'-\underset{\underset{O}{\|}}{P}-N-R_{1a}' \qquad \text{I'a}$$

in which
  both $R'_{1a}$'s are cyclohexyl, unsubstituted phenyl or phenyl substituted with up to 2 substituents selected from 1 or 2 chlorine atoms and 1 or 2 methyl and ethyl radicals and
  both $R'_{2a}$'s are a radical of formula $$-N\diagdown^{R_{3a}'}_{R_{4a}'}$$

wherein $R'_{3a}$ is hydrogen, methyl or ethyl, and
  $R'_{4a}$ is cyclohexyl, unsubstituted phenyl or phenyl substituted with up to 2 substituents selected from 1 or 2 chlorine atoms and 1 or 2 methyl and ethyl radicals, or
  $R'_{3a}$ and $R'_{4a}$, together with the common nitrogen atom, form a piperidino or morpholino ring,
with the proviso that when simultaneously $R'_{3a}$ is hydrogen and $R'_{1a}$ is unsubstituted or substituted phenyl, $R'_{4a}$ is only unsubstituted or substituted phenyl.

Of the compounds of formula I'a, a preferred class is constituted by those of formula I'b, $$R_{1b}'-N-\overset{\overset{O}{\|}}{P}-R_{2b}' \atop R_{2b}'-\underset{\underset{O}{\|}}{P}-N-R_{1b}' \qquad \text{I'b}$$

in which
  both $R'_{1b}$'s are unsubstituted phenyl or phenyl substituted with 1 or 2 chlorine atoms in the meta- and/or para-position(s) or a methyl radical, and
  both $R'_{2b}$'s are a radical of formula $$-N\diagdown^{R_{3b}'}_{R_{4b}'}$$

wherein $R'_{3b}$ is hydrogen or methyl and
  $R'_{4b}$, independently, has one of the significances of $R'_{1b}$.

Of the compounds of formula I'b, a preferred class is constituted by those of formula I'c, $$R_{1c}'-N-\overset{\overset{O}{\|}}{P}-R_{2c}' \atop R_{2c}'-\underset{\underset{O}{\|}}{P}-N-R_{1c}' \qquad \text{I'c}$$

in which
  both $R'_{1c}$'s are unsubstituted phenyl or phenyl substituted with a methyl radical, and
  both $R'_{2c}$'s are a radical of formula $-NHR'_{4c}$,
wherein
  $R'_{4c}$, independently, has one of the significances of $R'_{1c}$.

Of the compounds of formula I'', a preferred class is constituted by those of formula I''a, $$R_{1a}''-N-\overset{\overset{S}{\|}}{P}-R_{2a}'' \atop R_{2a}''-\underset{\underset{S}{\|}}{P}-N-R_{1a}'' \qquad \text{I''a}$$

in which
  both $R''_{1a}$'s are methyl, unsubstituted phenyl or phenyl substituted with 1 or 2 chlorine atoms, a $C_{1-2}$ alkyl or alkoxy radical, or a chlorine atom and a $C_{1-2}$ alkyl or alkoxy radical, and
  both $R''_{2a}$'s are a radical of the formula $$-N\diagdown^{R_{3a}''}_{R_{4a}''}$$

wherein
  $R''_{3a}$ is hydrogen, methyl or ethyl, and
  $R''_{4a}$ is $C_{1-6}$ alkyl, cyclohexyl, unsubstituted phenyl or phenyl substituted with up to 3 substituents selected from 1 or 2 chlorine atoms, a methyl radical and a methoxy radical, or
  $R''_{3a}$ and $R''_{4c}$, together with the common nitrogen atom, form a piperidino or morpholino ring.

Of the compounds of formula I''a, a preferred class is constituted by those of formula I''b, $$R_{1b}''-N-\overset{\overset{S}{\|}}{P}-R_{2b}'' \atop R_{2b}''-\underset{\underset{S}{\|}}{P}-N-R_{1b}'' \qquad \text{I''b}$$

in which
  both $R''_{1b}$'s are unsubstituted phenyl or phenyl substituted with 1 or 2 chlorine atoms in the meta- and/or para-position(s), or a methyl or methoxy radical, and
  both $R''_{2b}$'s are a radical of formula

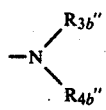

wherein
R"$_{3b}$ is hydrogen, methyl or ethyl, and
R"$_{4b}$ is C$_{1-6}$ alkyl, cyclohexyl, unsubstituted phenyl or phenyl substituted with 1 or 2 chlorine atoms in the meta- and/or para-position(s), or a methyl or methoxy radical, or
R"$_{3b}$ and R"$_{4b}$, together with the common nitrogen atom, form a piperidino ring.

Of the compounds of formula I"b, a preferred class is constituted by those of formula I"c,

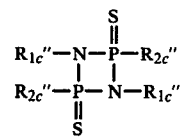

in which
both R"$_{1c}$'s are unsubstituted phenyl or phenyl substituted with a chlorine atom in the meta- or para-position or a methyl radical, and
both R"$_{2c}$'s are a radical of formula —NH—R"$_{4c}$, wherein R"$_{4c}$, independently, has one of the significances of R"$_{1c}$.

Examples of compounds of formula I are the following:

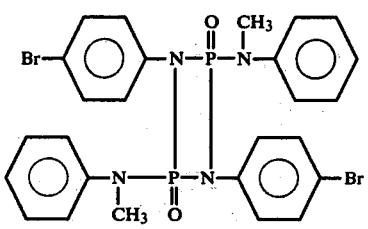
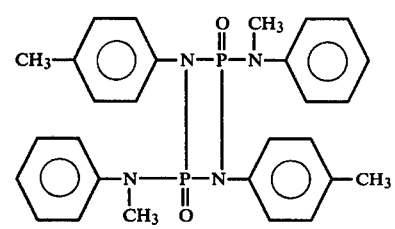
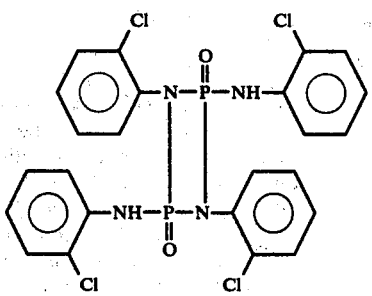
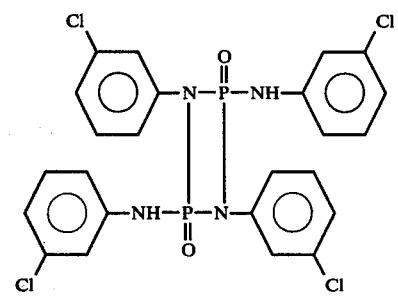
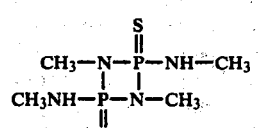
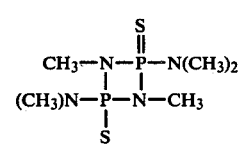
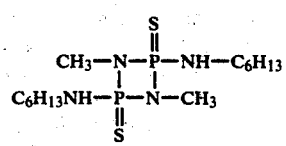
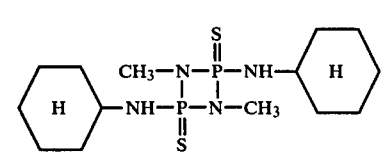
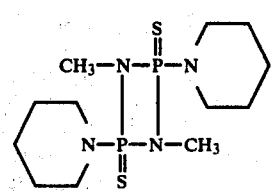
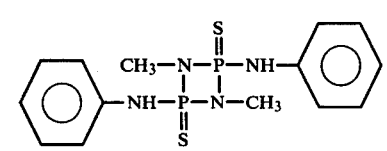

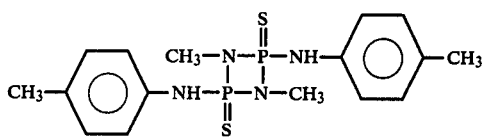

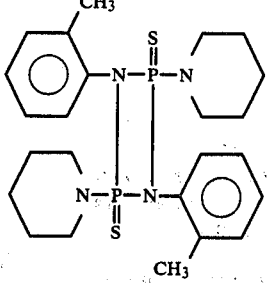

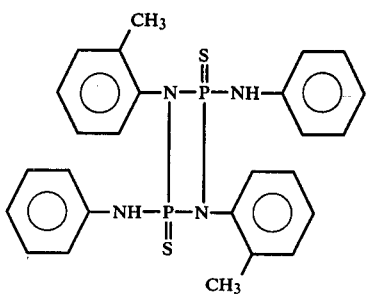

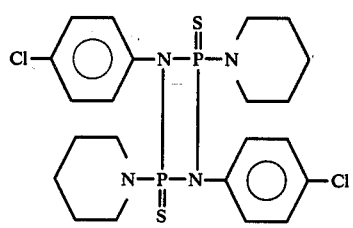

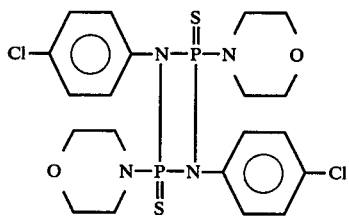

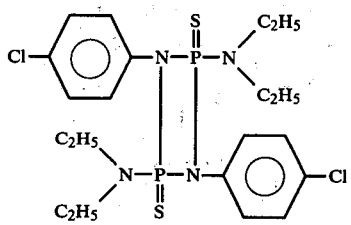

The production of compounds of formula I is known. Those of formula I' may be produced, for example, according to the processes described in Liebig's Annalen der Chemie 407, 311–316 (1915) and in Berichte 29, 716 (1896), whereas those of formula I" may be produced, for example, according to the processes described in Houben-Weyl, Methoden der Organischen Chemie, 4th Edition, Vol. 12/II, 978–981 or in Zeitschrift für Anorganische und Allgemeine Chemie 343, 154–164 (1966).

The present invention further provides a method for the production of flameproofed, regenerated cellulose comprising regenerating cellulose from its solution, e.g. viscose, containing a compound of formula I, as defined above. The term "regenerated cellulose" is well understood in the art to which it pertains. Amongst the procedures for producing regenerated cellulose are those involving the formation at one stage of alkali cellulose xanthate or a tetramine cupric hydroxide complex of cellulose, and such procedures are so adapted according to the present invention to include the regeneration of cellulose from its solution containing the compound of formula I as a flameproofing agent. Preferably the cellulose is regenerated from an alkali cellulose xanthate solution.

Prior to the regeneration of cellulose, cellulose is brought into solution, e.g. by such known processes as converting it into a soluble derivative by the xanthate method or through formation of the tetramine cupric hydroxide complex thereof. The compound of formula I is then added to the cellulose solution, for example by itself or as a fine dispersion in water, preferably the latter. When added alone, the compound may be introduced into the cellulose solution either continuously or discontinuously, i.e. in batches, and thereafter vigorous stirring of the cellulose solution containing the compound of formula I may be applied to distribute the latter uniformly in the solution. The same technique may also be adopted for the addition of an aqueous dispersion of the compound. Preferably the aqueous dispersion has a concentration by weight of compound in dispersion of 15 to 30%, or more preferably 20 to 25%. In all cases it can be advantageous to add conventional dispersion stabilisers and/or dispersion agents to the cellulose medium to promote uniformity of distribution of the compound in the cellulose solution. The weight of compound of formula I present in the cellulose solution for which regenerated cellulose is to be formed is preferably in the range 10 to 35%, or more preferably 15 to 25% of the weight of the cellulose starting material, e.g. α-cellulose. Accordingly, the flameproofed regenerated cellulose of the present invention preferably contains 10 to 35%, or more preferably 15 to 25% by weight, with respect to the weight of cellulose starting material, of compound of formula I.

Other flameproofing compounds, e.g. reaction products of a phosphorus nitrile chloride with glycols may be added to the cellulose solution as well as a compound of formula I. Such other suitable flameproofing compounds include the products of reactions between a phosphorus nitrile chloride and neopentyl glycol or other glycols, as described in German Offenlegungsschrift No. 2,316,959. In a preferred embodiment of the present invention, flameproofed regenerated cellulose contains as the flameproofing agents a compound of formula I and the reaction product of a phosphorus nitrile chloride and a glycol, preferably neopentyl glycol. Preferably, the amount of this additional flameproofing agent when employed is up to 90% by weight of the total flameproofing agent present, more preferably in the range 10 to 70%, and especially in the range 15 to 60%.

The regenerated cellulose may be in the form of filaments and sheets. Apart from flame-resistance, the so-produced flameproofed regenerated cellulose possesses its normal technically important properties which are only slightly affected by the presence of the incorporated flameproofing agents.

The following Examples (a) to (h) illustrate the preparation of various flameproofing compounds of formula I useable in the flameproofed, regenerated cellulose and the method of production thereof of the present invention, and further such compounds are given in Tables 1 and 2 which follow the Examples. Examples 1 and 2 illustrate the method and the flameproofed, regenerated cellulose of the present invention. In the examples, the parts and percentages are by weight and the degrees are in Centigrade.

PRODUCTION OF FLAMEPROOFING COMPOUNDS OF FORMULA I (a) Production of the compound of formula

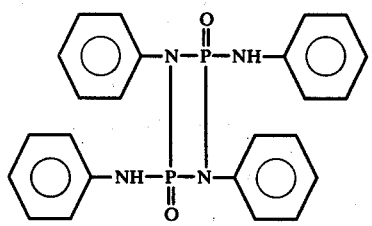
(a)

14.2 parts of phosphorus oxychloride and 24 parts of finely ground aniline hydrochloride in 100 parts of xylene are placed in a stirring vessel consisting of material which is resistant to hydrogen chloride and having an internal thermometer and reflux condenser. The mixture is first heated with good stirring to 120°, with a slight current of nitrogen and moisture excluded, and is kept at this temperature for 15 hours. Subsequently, it is heated to reflux (internal temperature 135°). The reaction, with hydrogen chloride removed, is completed after a further 45 hours. It is then cooled to room temperature and the solid substance formed during the reaction is filtered off. The substance is extracted with boiling water and subsequently dried. 19 parts of a white solid are obtained, which consists of the flame-resistant material. Its melting point is 360°–362° This active material may be used in the form of an aqueous dispersion, for the production of low-flammable materials of regenerated cellulose. In a similar manner, the compounds nos. 1, 3, 5 and 6 of Table 1 are produced.

(b) Production of the compound of formula

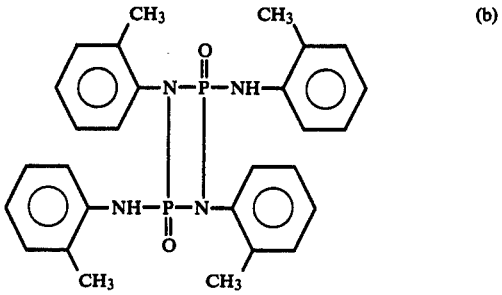
(b)

14.2 parts of phosphorus oxychloride and 26.6 parts of finely ground ortho-toluidine-hydrochloride in 100 parts of o-dichlorobenzene are placed in a stirring vessel consisting of material which is resistant to hydrogen chloride and having an internal thermometer and reflux condenser. The mixture is first heated with good stirring over the course of 30 minutes to 140° with a slight current of nitrogen and with moisture excluded, and it is kept at this temperature for 7 hours. Subsequently, it is heated to reflux (internal temperature 174°–180°). The reaction, with hydrogen chloride removed, is completed after a further 25 hours. It is then cooled to room temperature and the solid substance formed during the reaction is filtered off. The substance is extracted with boiling water and subsequently dried. 21 parts of a white solid are obtained, which consists of the flame-resistant material. Its melting point is 311°–314° C. This active material may be used in the form of an aqueous dispersion for the production of low-flammable materials of regenerated cellulose. In a similar manner, the compounds nos. 2, 4, 8, 9 and 10 of Table 1 are produced.

(c) Production of the compound of formula

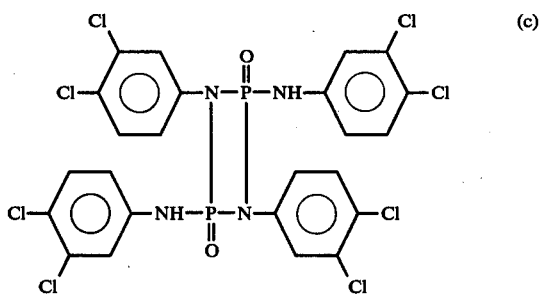
(c)

14.2 parts of phosphorus oxychloride and 16 parts of xylene are placed in a stirring vessel consisting of material which is resistant to hydrogen chloride and having an internal thermometer and reflux condenser, and the mixture is cooled to about 3° with good stirring. With a slight current of nitrogen and with moisture excluded, 30 parts of 3,4-dichloroaniline are dissolved in 80 parts of xylene and are added over the course of 50 minutes in drops at 0° to 10°. Subsequently, it is heated to 115° and kept at this temperature for 4 hours. It is then heated to reflux (internal temperature 135°). The reaction, with hydrogen chloride removed, is completed after a further 24 hours. It is then cooled to room temperature and the solid substance formed during the reaction is filtered off. The product is then extracted with boiling water and subsequently dried. 30 parts of a white solid are obtained, which consists of the flame-resistant material. Its melting point is >360° C. In a similar manner, compound no. 7 of Table 1 is produced.

(d) Production of the compound of formula

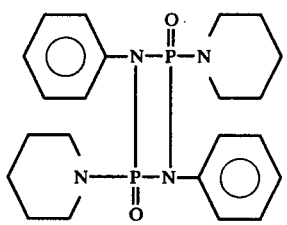

(d,a) 160 parts of phosphorus oxychloride and 430 parts of xylene are placed in a stirring vessel. With good stirring and with a slight current of nitrogen, 170 parts of piperidine dissolved in 430 parts of xylene are added in drops at 0° to 50° over the course of 90 minutes. Subsequently, the reaction mixture is heated to 85° and is kept at this temperature for 3 hours. The piperidine hydrochloride formed during the reaction is filtered off, the filtrate is concentrated and the resulting yellow oil is distilled at 124°–128°/11 mm Hg. 96.5 parts of colourless oil consisting of the compound of formula

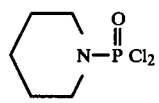

are obtained.

(d,b) 80 parts of o-dichlorobenzene, 48 parts of aniline hydrochloride and 75 parts of the above compound (d.a) are mixed in a stirring vessel and are heated to 100° with good stirring and a slight current of nitrogen. The reaction mixture is kept at this temperature for 8 hours and it is then heated to 175° to 180°. After 40 hours at this temperature, the reaction is completed. The reaction mixture is cooled and the separated solid is filtered off and dried. The crystal powder obtained is suspended in water, then filtered and dried. About 70 parts of the white solid compound (d) are obtained, and this is further purified by recrystallisation from alcohol. Its melting point is 230°–231° C. In a similar manner, the compounds listed in Table 2 are produced.

(e) Production of the compound of formula

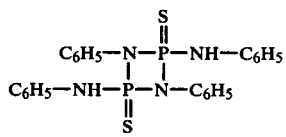

45.7 parts of thiophosphoryl chloride (PSCl₃), 235 parts of xylene and 70 parts of aniline hydrochloride are mixed in a stirring vessel and are heated to 120° with a slight current of nitrogen. The mixture is kept at this temperature for 15 hours and is subsequently heated at 135° for a further 45 hours. After the reaction has been completed, the mixture is cooled, the separated solid is filtered off and dried. The crystal powder obtained is suspended in dilute hydrochloric acid, then filtered and washed to neutral with water. About 50 parts of a compound of formula (e) are obtained, which is further purified by recrystallisation from chlorobenzene. However, recrystallisation is not necessary for the production according to the invention of low-flammable, regenerated cellulose. The product consists of a white solid having a melting point of 243°–246°. In a similar manner, the compound of formula

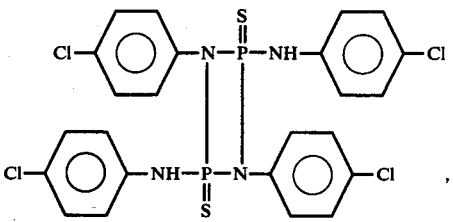

having a melting point of 238°–240° C., is produced by starting with 67.8 parts of thiophosphoryl chloride, 610 parts of xylene and 131.2 parts of p-chloroaniline hydrochloride. In a similar manner, the compounds of formula

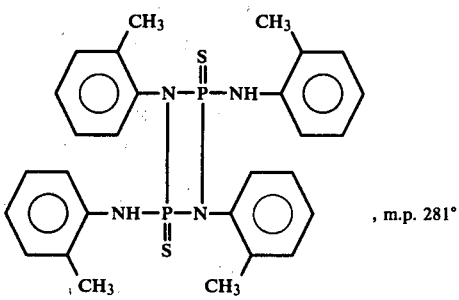
, m.p. 281° and

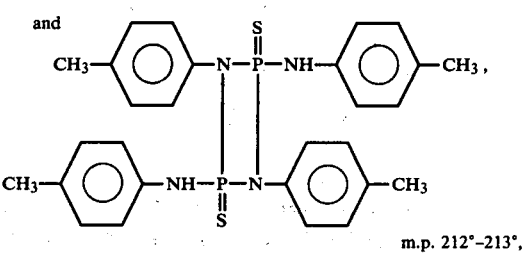
m.p. 212°–213°, are produced, by starting with 33.9 parts of thiophosphoryl chloride, 300 parts of xylene and 57.4 parts of ortho- or para-toluidine hydrochloride.

(f) Production of the compound of formula (f)

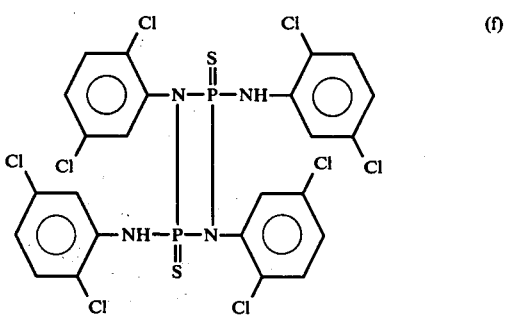

33.9 parts of thiophosphoryl chloride, 110 parts of orthodichlorobenzene and 79.4 parts of 2,5-dichloroaniline hydrochloride are mixed in a stirring vessel and are heated slowly with a current of nitrogen to 150°. The mixture is kept at this temperature for 15 hours and is subsequently heated for 8 hours to 175°. It is then cooled, the reaction mixture is freed in a vacuum from the solvent and the product required is obtained by recrystallisation several times from chlorobenzene. Its melting point is 253°–256°.

In a similar manner, the compound of formula

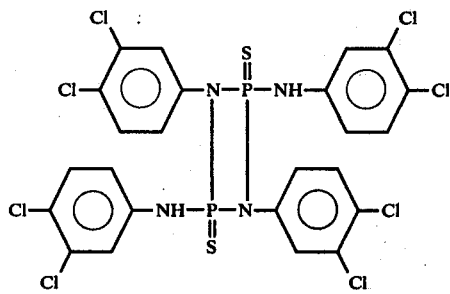

having a melting point of 223°–226° is produced, starting in this case with 3,4-dichloroaniline hydrochloride.

(g) Production of the compound of formula (g)

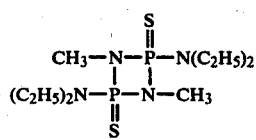
(g)

13 parts of 2,4-dithio-2,4-dichloro-1,3-dimethyl-cyclodiphosphazene of formula

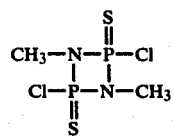

are dissolved in 400 parts of benzene in a stirring vessel and a solution of 15 parts of diethylamine in 170 parts of benzene is added at 20° over the course of 20 minutes. The mixture is kept at room temperature for 24 hours and is subsequently filtered. The filtrate is concentrated and cooled, whereupon the desired product is crystallised out. The melting point is 168°–170°.

(h) Production of the compound of formula (h)

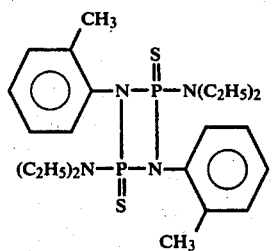
(h)

10.2 parts of 2,4-dithio-2,4-dichloro-1,3-bis(2-methylphenyl)-cyclodiphosphazene of formula

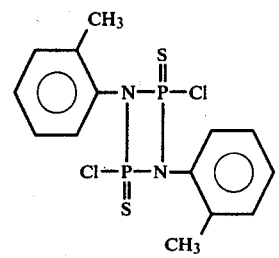

are suspended in 60 parts of benzene in a stirring vessel, and 8 parts of diethylamine are added in drops at 20° over the course of 4 minutes. The mixture is kept at 20° for 4 hours with a slight external cooling and is subsequently heated for 2 hours at reflux temperature. The reaction mixture is cooled, separated from the salt by filtration and freed from benzene in a vacuum. The desired product is obtained from the residue by recrystallisation from alcohol. Its melting point is 168°–171°.

Table 1

$$\begin{array}{c} O \\ \| \\ X-N-P-NH-X \\ | \qquad | \\ X-NH-P-N-X \\ \| \\ O \end{array}$$

| No. | X | m.p. °C. |
|-----|---|----------|
| 1 | H$_3$C—⟨phenyl⟩— (4-methylphenyl) | 325–328 |
| 2 | H$_3$C—⟨phenyl⟩—CH$_3$ (3,4-dimethylphenyl) | 304–307 |
| 3 | H$_3$C, H$_3$C—⟨phenyl⟩—CH$_3$ (trimethylphenyl) | 358–360 |
| 4 | CH$_3$—⟨phenyl⟩—CH$_3$ (2,6-dimethylphenyl) | >360 |
| 5 | H$_3$CO—⟨phenyl⟩— (4-methoxyphenyl) | 320–322 |
| 6 | Br—⟨phenyl⟩— (4-bromophenyl) | >360 |
| 7 | Cl—⟨phenyl⟩— (4-chlorophenyl) | >360 |
| 8 | Cl—⟨phenyl⟩—Cl (3,4-dichlorophenyl) | 290–293 |

Table 1-continued $$\begin{array}{c} \quad\;\; O \\ \quad\;\; \| \\ X-N-P-NH-X \\ \;\;|\quad\;\;\;| \\ X-NH-P-N-X \\ \quad\;\; \| \\ \quad\;\; O \end{array}$$

| No. | X | m.p. °C. |
|---|---|---|
| 9 | 2,4-dichlorophenyl | 298–301 |
| 10 | 2,6-dichlorophenyl | >360 |
| 11 | cyclohexyl (H) | >360 |

Table 2

$$\begin{array}{c} \quad\;\; O \\ \quad\;\; \| \\ R_1-N-P-R_2 \\ \;\;|\quad\;\;\;| \\ R_2-P-N-R_1 \\ \quad\;\; \| \\ \quad\;\; O \end{array}$$

| No. | R₁ | R₂ | m.p. °C. |
|---|---|---|---|
| 12 | phenyl | –N(C₃H₇)₂ | 173–174 |
| 13 | phenyl | –N(CH₃)(phenyl-H) | 315–316 |
| 14 | 4-chlorophenyl | piperidino | 273–275 |
| 15 | 2,4-dichlorophenyl | piperidino | 254–256 |
| 16 | 2,4,6-trichlorophenyl | piperidino | 232–233 |
| 17 | 4-chlorophenyl | morpholino | 265–267 |
| 18 | phenyl | –N(CH₃)(phenyl) | 227–228 |
| 19 | 4-chlorophenyl | –N(CH₃)(phenyl) | 293–296 |
| 20 | 2,4-dichlorophenyl | –N(CH₃)(phenyl) | 257–258 |
| 21 | 2-methylphenyl | –N(CH₃)(phenyl) | 186–187 |

Production of Flameproofed Regenerated Cellulose

Example 1

15 Parts of the flameproofing compound of formula (a) are ground to a powder during 4 hours with 3.75 parts of a dispersion agent based on sodium naphthalene sulphonate and 56.25 parts of water by revolution at the rate of 1500 revolutions per minute in the presence of 75 parts of quartzite beads, cooling with ice being maintained throughout the grinding. The quartzite beads are removed by filtration and 67 parts of an aqueous dispersion containing 20% of flameproofing compound are obtained.

18 Parts of the aqueous dispersion are introduced with stirring into 200 parts of a cellulose xanthate solution containing 18 parts of α-cellulose. The solution is forced through nozzles by a conventional spinning process into a precipitation bath containing per liter 125 g of sulphonic acid, 240 g of anhydrous sodium sulphate and 12 g of anhydrous zinc sulphate. The resulting fibres are washed thoroughly and formed into knit fabrics, which are subsequently tested for flame-resistance by the Fenimore and Martin testing procedure, described in Modern Plastics, November 1966, involving the determination of the oxygen limit value (LOI). The results are compared with those given by untreated regenerated cellulose to establish the flameproofing property imparted by the incorporated formula (a) compound.

In a similar manner, the flameproofed regenerated cellulose containing the other compounds of formula I, described in Examples b) to h) and Tables 1 and 2, hereinbefore, is produced.

Example 2

In sequence, 9 parts of a 20% aqueous dispersion of the flameproofing compound of formula (a) (produced as described in Example 1) and 5.15 parts of a 35% aqueous dispersion of the reaction product of oligomeric phosphorus nitrile chlorides and 2,2-dimethyl-1,3-propanediol (produced as described in Example 4 of German Offenlegungsschrift No. 2,316,959) are introduced with stirring into 200 parts of a cellulose xanthate solution containing 18 parts of α-cellulose.

The subsequent procedure for producing and testing the flameproof finished regenerated cellulose is the same as described in Example 1.

What is claimed is:

1. Flameproofed regenerated cellulose containing as a flameproofing agent a compound of formula,

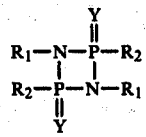

in which
both Y's are oxygen or sulphur,
both $R_1$'s are unsubstituted phenyl or phenyl substituted with up to 3 substituents selected from 1 to 3 chlorine atoms, a bromine atom in the para-position, 1 to 3 $C_{1-4}$ alkyl radicals and 1 to 3 $C_{1-4}$ alkoxy radicals, the aggregate of the carbon atoms in the alkyl and/or alkoxy radicals being a maximum of 4, and, when Y is sulphur, both $R_1$'s may also be methyl, and
both $R_2$'s are a radical of formula

wherein $R_3$ is hydrogen and
$R_4$ is unsubstituted phenyl or phenyl substituted with up to 3 substituents selected from 1 to 3 chlorine atoms, a bromine atom in the para-position, 1 to 3 $C_{1-4}$ alkyl radicals and 1 to 3 $C_{1-4}$ alkoxy radicals, the aggregate of the carbon atoms in the alkyl and/or alkoxy radicals being a maximum of 4, or, when Y is oxygen, $R_4$ can be cyclohexyl, or when
Y is oxygen $R_3$ and $R_4$, together with the common nitrogen atom and optionally with a further hetero atom, form a saturated 5- or 6-membered heterocyclic ring,
with the proviso that when simultaneously Y is oxygen, $R_3$ is hydrogen and $R_1$ is unsubstituted or substituted phenyl, $R_4$ is only unsubstituted or substituted phenyl.

2. Flameproofed regenerated cellulose in which the flameproofing agent is a compound of formula,

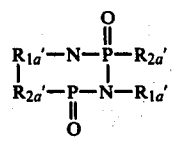

in which
both $R'_{1a}$'s are cyclohexyl, unsubstituted phenyl or phenyl substituted with up to 2 substituents selected from 1 to 2 chlorine and 1 or 2 methyl and ethyl radicals and
both $R'_{2a}$'s are a radical of formula

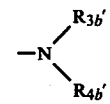

wherein $R'_{3a}$ is hydrogen, methyl or ethyl, and
$R'_{4a}$ is cyclohexyl, unsubstituted phenyl or phenyl substituted with up to 2 substituents selected from 1 or 2 chlorine atoms and 1 or 2 methyl and ethyl radicals, or
$R'_{3a}$ and $R'_{4a}$, together with the common nitrogen atom, form a piperidino or morpholino ring,
with the proviso that when simultaneously $R'_{3a}$ is hydrogen and $R'_{1a}$ is unsubstituted or substituted phenyl, $R'_{4a}$ is only unsubstituted or substituted phenyl.

3. Flameproofed, regenerated cellulose according to claim 2, in which the flameproofing agent is a compound of formula,

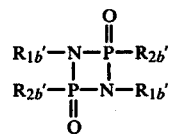

in which
both $R'_{1b}$'s are unsubstituted phenyl or phenyl substituted with 1 or 2 chlorine atoms in the meta- and/or paraposition(s) or a methyl radical, and
both $R'_{2b}$'s are a radical of formula

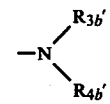

wherein $R'_{3b}$ is hydrogen or methyl and
$R'_{4b}$, independently, has one of the significances of $R'_{1b}$.

4. Flameproofed, regenerated cellulose according to claim 3, in which the flameproofing agent is a compound of formula,

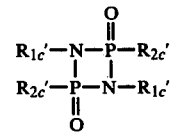

in which
both $R'_{1c}$'s are unsubstituted phenyl or phenyl substituted with a methyl radical, and
both $R'_{2c}$'s are a radical of formula $-NHR'_{4c}$, wherein $R'_{4c}$, independently, has one of the significances of $R'_{1c}$.

5. Flameproofed, regenerated cellulose in which the flamproofing agent is a compound of formula,

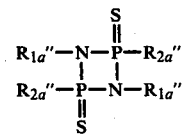

in which both R″$_{1a}$'s are methyl, unsubstituted phenyl or phenyl substituted with 1 or 2 chlorine atoms, a C$_{1-2}$ alkyl or alkoxy radical, or a chlorine atom and a C$_{1-2}$ alkoxy or alkoxy radical, and both R″$_{2a}$'s are a radical of formula

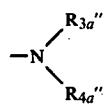

wherein R″$_{3a}$ is hydrogen, methyl or ethyl, and

R″$_{4a}$ is C$_{1-6}$ alkyl, cyclohexyl, unsubstituted phenyl or phenyl substituted with up to 3 substituents selected from 1 or 2 chlorine atoms, a methyl radical and a methoxy radical, or R″$_{3a}$ and R″$_{4a}$, together with the common nitrogen atom, form a piperidino or morpholino ring.

6. Flameproofed, regenerated cellulose according to claim 5, in which the flameproofing agent is a compound of formula,

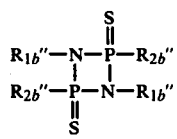

in which both R″$_{1b}$'s are unsubstituted phenyl or phenyl substituted with 1 or 2 chlorine atoms in the meta- and/or para-position(s), or a methyl or methoxy radical, and both R″$_{2b}$'s are a radical of formula

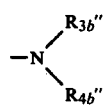

wherein R″$_{3b}$ is hydrogen, methyl or ethyl, and

R″$_{4b}$ is C$_{1-6}$ alkyl, cyclohexyl, unsubstituted phenyl or phenyl substituted with 1 or 2 chlorine atoms in the meta- and/or para-position(s), or a methyl or methoxy radical, or R′$_{3b}$ and R″$_{4b}$, together with the common nitrogen atom, form a piperidino ring.

7. Flameproofed, generated cellulose according to claim 6, in which the flameproofing agent is a compound of formula,

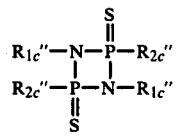

in which both R″$_{1c}$'s are unsubstituted phenyl or phenyl substituted with a chlorine atom in the meta- or para-position or a methyl radical, and both R″$_{2c}$'s are a radical of formula —NH—R″$_{4c}$, wherein R″$_{4c}$, independently, has one of the significances of R″$_{1c}$.

8. Flameproofed, regenerated cellulose according to claim 4, in which the flameproofing agent is a compound of the formula,

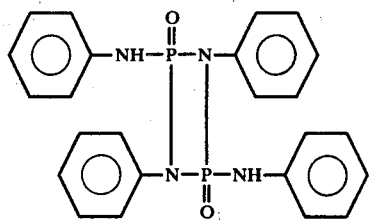

9. Flameproofed, regenerated cellulose according to claim 4, in which the flameproofing agent is a compound of the formula,

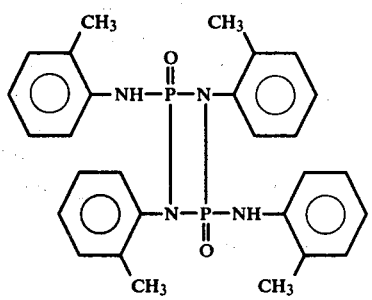

10. Flameproofed, regenerated cellulose according to claim 3, in which the flameproofing agent is a compound of the formula,

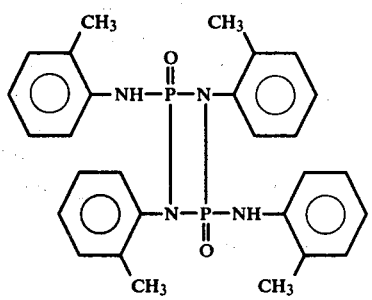

11. Flameproofed, regenerated cellulose according to claim 3, in which the flameproofing agent is a compound of the formula,

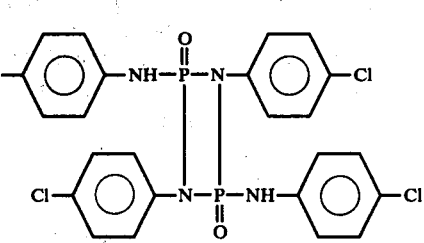

12. Flameproofed, regenerated cellulose according to claim 2, in which the flameproofing agent is a compound of the formula,

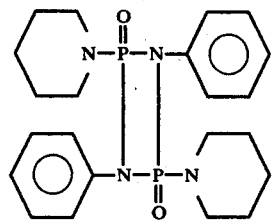

13. Flameproofed, regenerated cellulose according to claim 3, in which the flameproofing agent is a compound of the formula,

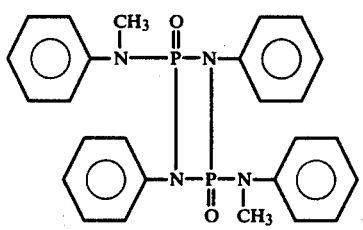

14. Flameproofed, regenerated cellulose according to claim 1, which contains 10 to 35% by weight, with respect to the weight of cellulose starting material, of the flameproofing agent.

15. Flameproofed, regenerated cellulose according to claim 1, which contains as a further flameproofing agent the reaction product of a phosphorus nitrile chloride and a glycol.

16. A method for the production of flameproofed regenerated cellulose comprising regenerating cellulose from cellulose solution containing a compound as defined in claim 1.

17. A method according to claim 16 which includes the step of adding to the cellulose solution the compound as a fine dispersion in water.

18. A method according to claim 17, in which the aqueous dispersion has a concentration by weight of compound in dispersion of 15 to 30%.

19. A method according to claim 16 in which the weight of compound present in the cellulose solution from which flameproofed regenerated cellulose is to be formed is in the range 10 to 35% of the weight of the cellulose starting material present.

20. A method according to claim 16 in which the cellulose solution from which flameproofed regenerated cellulose is to be formed, contains a dispersion stabiliser and/or a dispersion agent.

* * * * *

UNITED STATES PATENT AND TRADEMARK OFFICE
CERTIFICATE OF CORRECTION

PATENT NO. : 4,210,451
DATED : July 1, 1980
INVENTOR(S) : Claudine Mauric/Rainer Wolf It is certified that error appears in the above—identified patent and that said Letters Patent is hereby corrected as shown below:

Column 17, Claim 2, line 52; after the word "Flameproofed" insert a comma.

Column 19, Claim 5, line 4; delete the word "alkoxy" (first occurrence) and insert in its place the word --alkyl--.

Column 19, Claim 6, lines 36-40; change $$"\ -N\!\!<^{R_{3b}}_{R_{4b}}"\quad \text{to} \quad --\ -N\!\!<^{R''_{3b}}_{R''_{4b}}\ --.$$

Column 19, Claim 6, line 46; delete the term "$R'_{3b}$" and insert in its place --$R''_{3b}$--.

Signed and Sealed this

*Twenty-fourth* Day of *August 1982*

|SEAL|

*Attest:*

GERALD J. MOSSINGHOFF

*Attesting Officer*    *Commissioner of Patents and Trademarks*